United States Patent
Hess et al.

(10) Patent No.: US 8,016,209 B2
(45) Date of Patent: Sep. 13, 2011

(54) LIQUID DROPLET PLUG AND SPRAY SYSTEM

(75) Inventors: Joseph Hess, Bevaix (CH); Amir Feriani, Auvernier (CH); Philippe Luginbuhl, Nods (CH); Raphaël Weber, Corcelles (CH)

(73) Assignee: EP Systems SA, Neuchâtel (CH)

( * ) Notice: Subject to any disclaimer, the term of this patent is extended or adjusted under 35 U.S.C. 154(b) by 610 days.

(21) Appl. No.: 11/569,279

(22) PCT Filed: Jun. 7, 2005

(86) PCT No.: PCT/EP2005/006089
§ 371 (c)(1),
(2), (4) Date: Nov. 25, 2008

(87) PCT Pub. No.: WO2005/120613
PCT Pub. Date: Dec. 22, 2005

(65) Prior Publication Data
US 2009/0084867 A1    Apr. 2, 2009

(30) Foreign Application Priority Data

Jun. 9, 2004 (EP) .................................. 04013559

(51) Int. Cl.
*B05B 1/08* (2006.01)
*B05B 9/03* (2006.01)
*B05B 1/30* (2006.01)
*B05B 1/00* (2006.01)
*A61M 11/06* (2006.01)

(52) U.S. Cl. .................. 239/102.2; 239/102.1; 239/600; 239/569; 239/596; 239/302; 239/338

(58) Field of Classification Search ............... 239/102.2, 239/102.1, 569–582.1, 690–708, 86, 596, 239/600, 302–379
See application file for complete search history.

(56) References Cited

U.S. PATENT DOCUMENTS

| | | | | |
|---|---|---|---|---|
| 3,275,240 A | * | 9/1966 | Peaslee et al. | 239/61 |
| 5,152,456 A | * | 10/1992 | Ross et al. | 239/102.2 |
| 5,404,871 A | * | 4/1995 | Goodman et al. | 128/200.14 |
| 5,487,378 A | * | 1/1996 | Robertson et al. | 128/200.16 |

(Continued)

FOREIGN PATENT DOCUMENTS

EP    0 923 957 A1    6/1999

(Continued)

OTHER PUBLICATIONS

E-Mail from Elson Silva, "Respecting Hydrology Science—US Pat. Application 20090084867", ECOLAB, Inc., dated Sep. 13, 2010, Campinas, SP, Brazil, pp. 1-4.

(Continued)

*Primary Examiner* — Jason J Boeckmann
*Assistant Examiner* — Steven M Cernoch
(74) *Attorney, Agent, or Firm* — Griffin & Szipl, P.C.

(57) ABSTRACT

The present invention concerns a liquid droplet spray system for atomizing a liquid substance, comprising: a support having a central aperture (27), a liquid droplet spray device in which a space is provided, the space being arranged to receive the liquid substance, and including a nozzle body (28) covering the space such that the liquid substance may exit the space of the device by traversing the nozzle body (28) and the system by traversing the central aperture (27) of the support, a reservoir (33) for containing the liquid substance.

15 Claims, 10 Drawing Sheets

U.S. PATENT DOCUMENTS

| | | | | |
|---|---|---|---|---|
| 5,518,179 | A * | 5/1996 | Humberstone et al. | 239/102.2 |
| 5,632,445 | A * | 5/1997 | Dubruque | 239/102.2 |
| 5,637,815 | A * | 6/1997 | Takahata et al. | 75/236 |
| 5,749,519 | A * | 5/1998 | Miller | 239/44 |
| 6,062,212 | A * | 5/2000 | Davison et al. | 128/200.16 |
| 6,196,219 | B1 * | 3/2001 | Hess et al. | 128/200.21 |
| 6,540,153 | B1 * | 4/2003 | Ivri | 239/4 |
| 6,651,650 | B1 * | 11/2003 | Yamamoto et al. | 128/200.16 |
| 6,978,941 | B2 * | 12/2005 | Litherland et al. | 239/4 |
| 7,694,892 | B2 * | 4/2010 | Feriani et al. | 239/102.2 |
| 2002/0023639 | A1 * | 2/2002 | Ivri et al. | 128/200.16 |
| 2002/0070239 | A1 * | 6/2002 | Garcia et al. | 222/199 |
| 2002/0185125 | A1 * | 12/2002 | Klimowicz et al. | 128/200.16 |

FOREIGN PATENT DOCUMENTS

| | | |
|---|---|---|
| EP | 1 005 916 A1 | 6/2000 |
| EP | 1 236 517 A1 | 9/2002 |
| EP | 1 559 436 A1 | 8/2005 |

OTHER PUBLICATIONS

International Search Report issued in corresponding application No. PCT/EP2005/006089, completed Jul. 22, 2005 and mailed Aug. 29, 2005.

* cited by examiner

LIQUID DROPLET PLUG AND SPRAY SYSTEM

This is a National Phase Application in the United States of International Patent Application No. PCT/EP2005/006089 filed Jun. 7, 2005, which claims priority on European Patent Application No. 04013559.2, filed Jun. 9, 2004. The entire disclosures of the above patent applications are hereby incorporated by reference.

FIELD OF THE INVENTION

The present invention relates to a liquid droplet plug & spray system comprising a liquid droplet spray device suitable for atomising a liquid substance, such as a personal or an ambient fragrance or a functional liquid such as an insecticide or a medicated liquid. Such a device may be used, e.g., for fragrance or functional or medical liquid dispensers, for an inhaler or the like, for controlled release of droplets of such. More specifically, the present invention concerns a liquid droplet spray system which is of modular design having a disposable part and a permanent, nondisposable part.

BACKGROUND OF THE INVENTION

Various devices are known for atomising a liquid. For example, the documents EP 0923957 and EP 1005916, both in the name of the present Applicant describe a liquid droplet spray device. A brief description of the liquid droplet spray device known from these documents, which are hereby incorporated by reference, is given here.

The spray device of the above-referenced documents consists of a housing formed of a superposition of a first substrate and a second substrate in-between which a space is formed for containing a liquid substance. One of the substrates contains outlet means containing outlet nozzles and output channels connecting these nozzles to the space. A liquid substance enters the spray device by way of, e.g., a very low pressure, e.g., around a few millibar or slightly negative pressure, or capillary action. This can be achieved for example by way of at least one input tube or needle through which the liquid substance may be supplied from an external reservoir into the spray device. The spray device further comprises a vibrating element, e.g. a piezoelectric element to cause vibration of the liquid substance in the space so as to cause the liquid to be ejected as a spray of droplets. There is no description of a system or of the arrangement of the external reservoir with respect to the device.

A liquid droplet spray system is known from the document U.S. Pat. No. 5,749,519. This device relates to an air freshener which has a reservoir for containing an air freshener liquid. The reservoir is connected to a vapour-emanating surface of a liquid dispensing device by way of a wick. The liquid is transmitted from the reservoir via the wick through capillary action to the vapour-emanating surface so as to dispense the air freshener.

Due to its design, and in particular due to the use of a wick, the liquid dispensing device always transmits the liquid to the vapour-emanating surface: Thus, to avoid waste and spill, the device is provided in a housing having a cover for sealing the vapour-emanating surface. Once the cover is removed, the vapour is dispensed into the surrounding air.

However, when the reservoir needs to be exchanged, the user will receive air freshener on his hands when manipulating the reservoir due to the wick being in contact with the liquid. Of course, air fresheners use strong fragrances so that this is not very pleasant. Further, this leads to a loss of liquid if one forgets to put the cover back on, and it is impossible to allow for a controlled dispersion of the vapour amount.

Another liquid droplet spray system is known from the document US 2002/0070239. This system has a reservoir, a flexible pouch, containing a porous material for absorbing the liquid of the reservoir. The reservoir is connected to a capillary channel, also containing a porous material, such as a wick. The channel leads the liquid to a perforated membrane surface. When the surface is vibrated by further provided vibration means, the liquid is dispensed as droplets.

Here again, a wick is used, both in the reservoir and in the capillary channel. Thus, when changing the reservoir, it would appear impossible to do such without any liquid spilling out.

Further, due to the design of the system, liquid may leak through the perforated membrane even when the system is not in use thus leading to wastage and related inconveniences such as unwanted fragrancing. Of course, controlled dispensing is not possible either with this system.

Another droplet spray device is known from the document U.S. Pat. No. 6,062,212 which describes a liquid dispenser having vibration means which are activated to expel liquid from a mesh in the usual manner, but which remain activated to ensure a complete emptying of the liquid from the dispenser. The disadvantage is that this additional atomising duration will sometimes be either too long or too short and that a fixed time will not work with liquids of various viscosities and surface tensions and ambient conditions.

Another droplet spray device is known from co-pending application no. EP 04 001 566.1 in the name of the present Applicant. This device consists of a disposable part having a reservoir for containing a liquid substance, and a valve for blocking the reservoir so as to avoid spill when the device is not in use, and a permanent, non-disposable part having the nozzle body, a piezo-electric actuator, electronic control means, and a fluidic interface linking the reservoir to the space in the nozzle body. Although this device overcomes many of the above-raised inconveniences due to partly disposable items, it suffers from contamination of the space of the droplet spray device, which may in certain cases not be fully emptied after use. A re-fill with another liquid substance will thus result in uncontrolled release, either in quantity or in actual substance caused by contamination.

Further, due to the presence of any remaining liquid substance, clogging may occur of the fluidic channel, of nozzles in the nozzle body or even of the reservoir thus impeaching the operation of the device.

It is, therefore, an object of the present invention to provide a liquid droplet spray system that overcomes the above-mentioned inconveniences and that can be efficiently used for liquid substances such as perfumes or other non-aqueous solvent based liquids, or for liquid medicaments.

It is another object of the present invention to provide such a system that is simple, reliable and inexpensive to manufacture, small in size and low in energy consumption and cost, and as such suitable as a personal or ambient fragrance and functional liquid dispenser.

SUMMARY OF THE INVENTION

Thus, the present invention concerns a liquid droplet spray system as defined in the appended claims.

Thanks to the construction of the liquid droplet spray system according to the present invention an efficient system may be obtained in a relatively simple and inexpensive manner.

Furthermore, due to the modular design of the system, it is possible to easily exchange the reservoir and nozzle body without any unwanted spill or wastage of liquid contained in the reservoir and without any risk of unwanted clogging. In fact, the system comprises a disposable part and a permanent, non-disposable part, wherein the disposable part comprises the reservoir containing the liquid substance, the nozzle body, a fluidic channel linking the reservoir to the space of the nozzle body as well as a valve ensuring that the disposable part is liquid tight even when removed from the system.

BRIEF DESCRIPTION OF THE DRAWINGS

Other features and advantages of the liquid droplet spray system according to the present invention will become clear from reading the following description, which is given solely by way of a non-limitative example thereby referring to the attached drawings in which.

DETAILED DESCRIPTION OF THE ILLUSTRATIVE EMBODIMENTS

An example of a preferred embodiment will now be described.

Figure 1A:
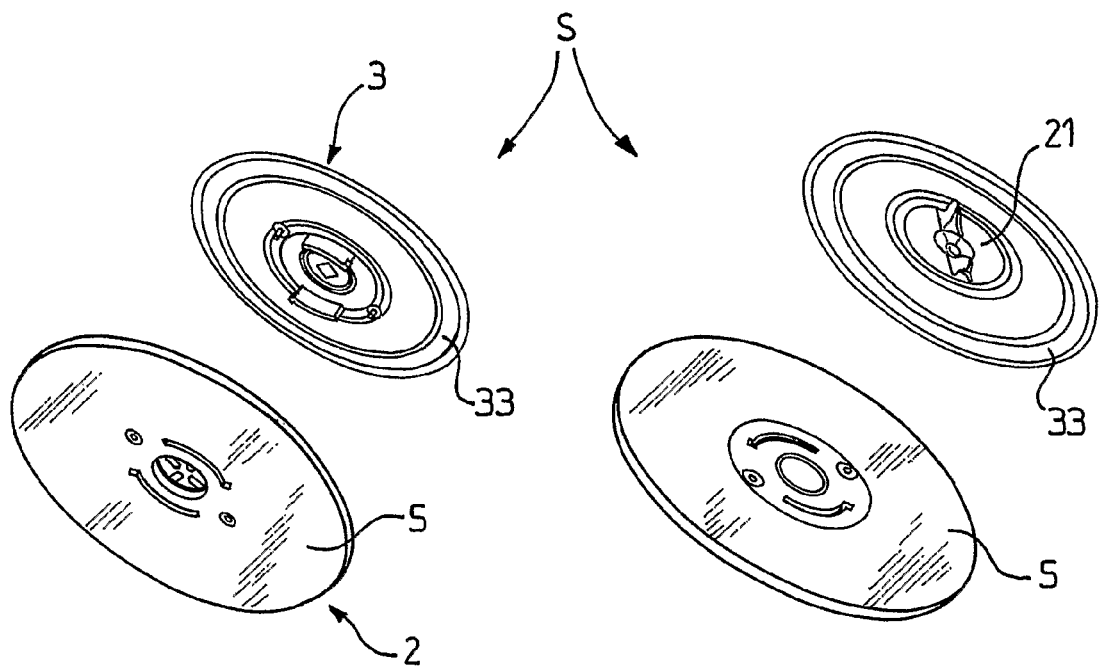
FIG. 1 shows a liquid droplet plug and spray system according to the present invention.
Figure 1B:
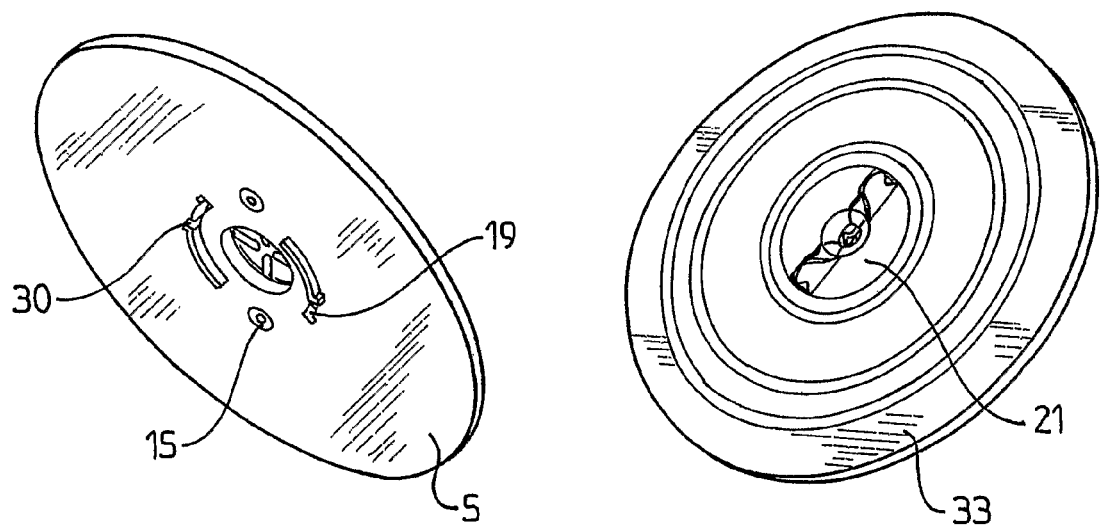

FIG. 1 shows a liquid droplet plug and spray system indicated by general reference S. This system contains a permanent, non-disposable part, and a disposable part. FIGS. 1a and 1b respectively show from below and from above a pre-assembly and a post-assembly view of the system.

Figure 2A:
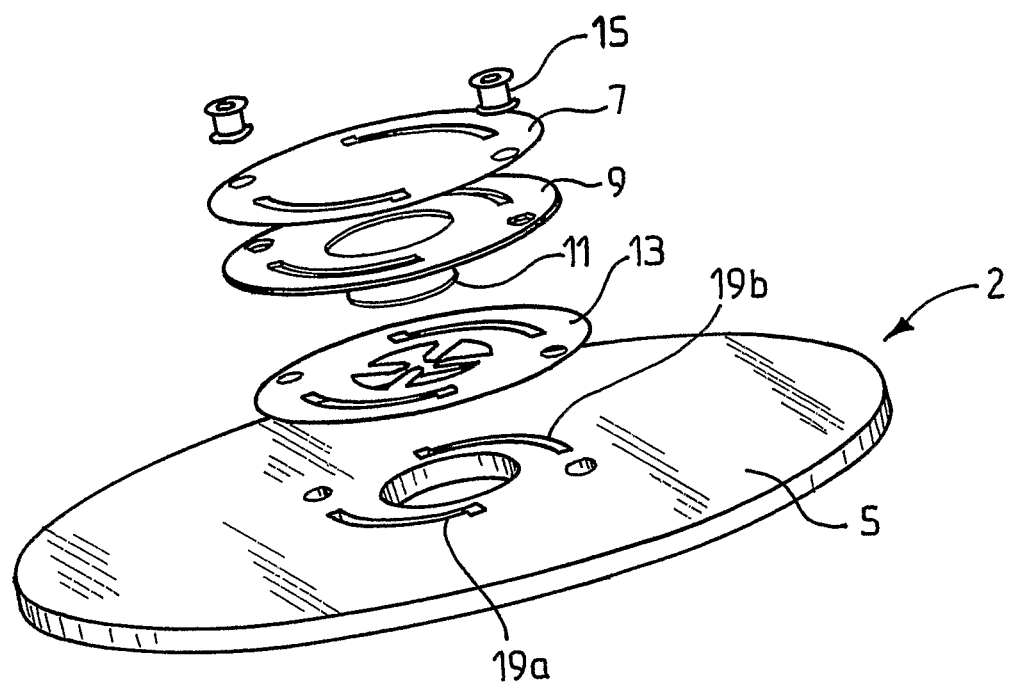
FIGS. 2a and 2b show an exploded view and an assembled view, respectively, of an example of a disk-shaped permanent part of the liquid droplet spray system of FIG. 1, FIGS. 3a and 3b show an exploded view and an assembled view, respectively, of an example of a valve body forming part of the disposable part of the liquid droplet spray system of FIG. 1.
Figure 2B:
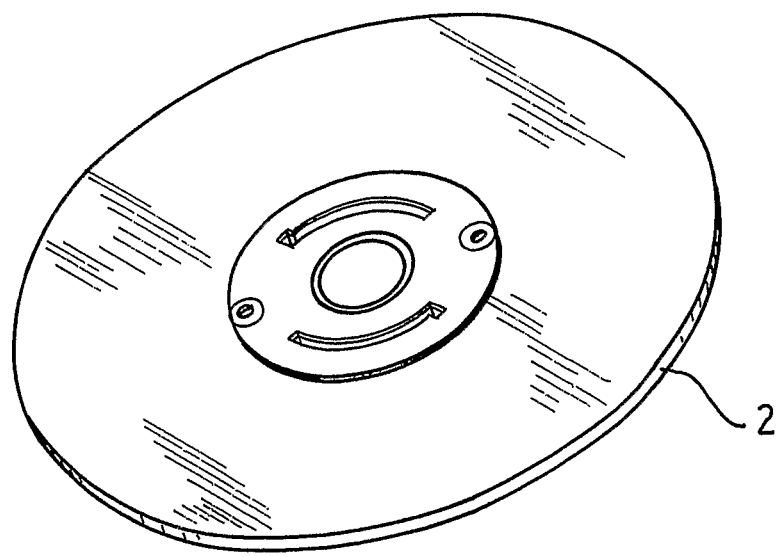

The permanent part comprises a support which may be a flexible electric circuit board or a PCB element, a membrane actuator, an insulator, an electromechanical actuator such as a piezoelectric element and an electrode. FIGS. 2a and 2b, respectively show an exploded view and an assembled view of an example of a disk-shaped permanent part, indicated by reference numeral 2, comprising a disk-shaped PCB 5, an electrode 13, a piezoelectric element 11, an insulator 9, and a membrane actuator 7, assembled one to the other by way of fastening means, here by way of rivets 15, to form a disk as shown in the assembled view in FIG. 2b. Of course the PCB is not always disc-shaped.

PCB 5 has an aperture 17 covered by piezoelectric element 11. Piezoelectric element further is electrically connected to both the membrane actuator 7 and electrode 13 which themselves are connected to the PCB, for example via rivets 15 as shown in FIG. 2A. In this example, PCB 5 further comprises two semicircular slots 19a and 19b for receiving notches provided on the disposable part, as will be explained further on.

The disposable part comprises a reservoir, a valve body, linked to the reservoir, a nozzle body linked to the valve body and may comprise an electrical power source such as a battery for powering the electrical control system. The permanent part comprises the electromechanical actuator (in this example the piezoelectric element), an electronic control means such as an ASIC and may comprise an electrical power source, such as a battery for powering the electronic control means and the electromechanical actuator.

Figure 3A:
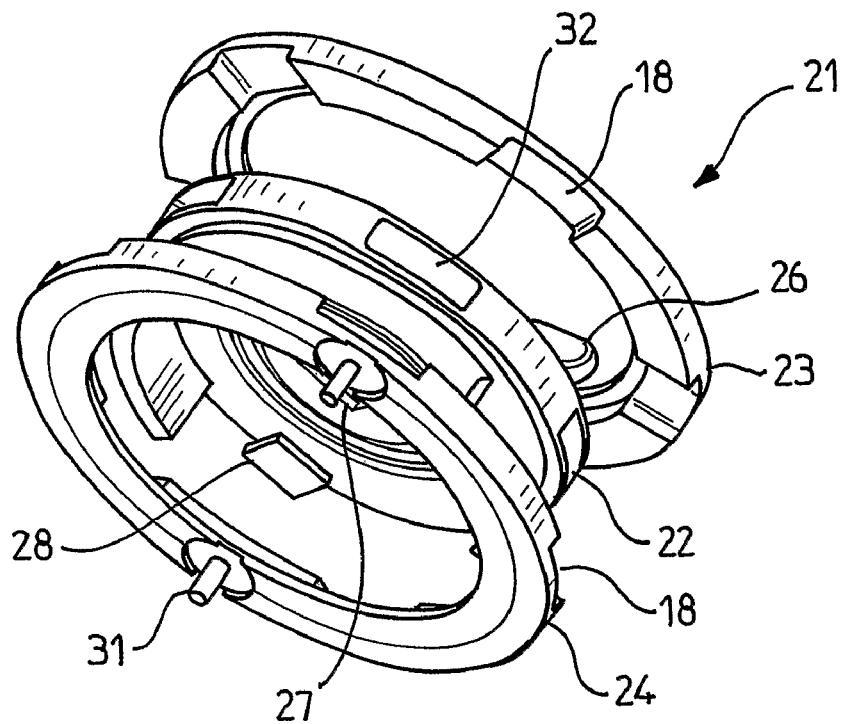
Figure 3B:
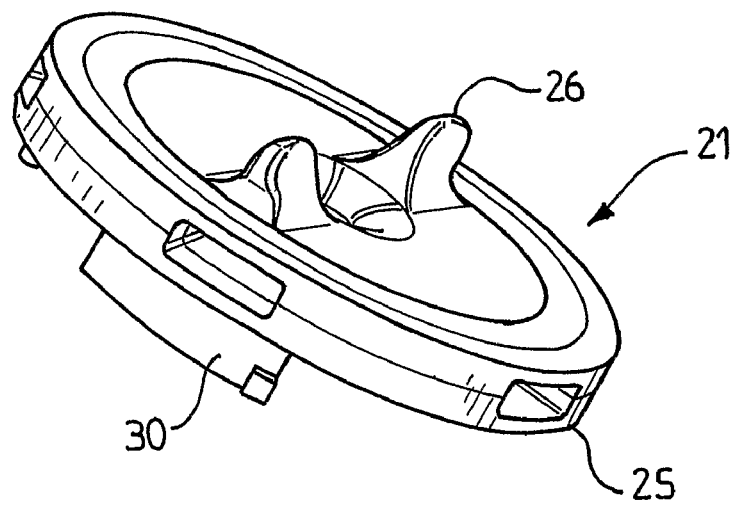

FIGS. 3a and 3b show an exploded view and an assembled view, respectively, of an example of a valve body of a valve body used in the disposable part of the liquid droplet plug and spray device according to the present invention.

Valve body 21 comprises a cylinder member 22 surrounded by a top ring member 23 and a bottom ring member 24. Cylinder member 22 is assembled with the ring members 23, 24 in such a way that it may rotate with respect to the ring members that are maintained in a fixed position. To this effect, cylinder member 24 is provided with a manipulating member on its top surface allowing to rotate it. In this example, the manipulating member consists of two projections 26. As can be seen in FIG. 3a, ring members 23 and 24 each have one or more slots 18 in their side surface and are assembled such that these slots are aligned to form apertures 25, see FIG. 3b, in the outer peripheral side surface of valve body 21. Cylinder member 22 also has one or more apertures in its side surface forming fluidic channels 32 through the cylinder member. By manipulating the projections 26, the fluidic channels 32 may be aligned or not with the side apertures 25 in the ring members.

Cylinder member 22 further has a central aperture 27 which is in fluidic connection with the fluidic channel(s) so as to allow for a flow of a liquid substance through the fluidic channel into the central aperture.

A nozzle body 28 is fitted over central aperture 27 on the bottom surface of valve body 21 so as to cover the central aperture. The bottom surface of cylinder member 22 is that surface that will be in contact with membrane actuator 7 of permanent part 2 when attached thereto. Nozzle body 28 may be made of a membrane having one or more perforations and covering central aperture 27 such that a liquid substance may exit the central aperture and the valve body by traversing the one or more perforations of the perforated membrane. Such perforate membrane may be made of for example a silicon array.

Valve body 21 further comprises on its bottom surface at its periphery two engagement notches 30 which are suitably arranged so as to fit into slots 19a and 19b of PCB 5 so as to allow for a rotational movement of the valve body when attached to the permanent part, as will be explained in more detail further on. Together, these slots and notches thus form joining and locking means allowing attachment of the disposable part to the permanent part. By selecting the length of the semi-circular slots 19a, 19b, the rotational movement of the valve body can be set. These engagement notches form part of the plug-in system allowing to plug the disposable part into permanent part 2 and to remove it again there from. Advantageously, these notches 30 may be formed as a BNC-type connectors so as to allow to fit valve body 21, and thus the disposable part to the permanent part 2 in a secure manner.

Further, bottom ring member 24 may be provided with two or more projections 31 arranged on its bottom surface, such to fit into a corresponding rivet of the permanent part 2 for fixing the disposable part into a predetermined position with respect to the permanent part. In an advantageous arrangement, these projections 31 may be conductive, so that when inserted into rivet 15, an electric connection may be established, for example by further linking rivet 15 to electrode 13 on permanent part 2.

Figure 5:
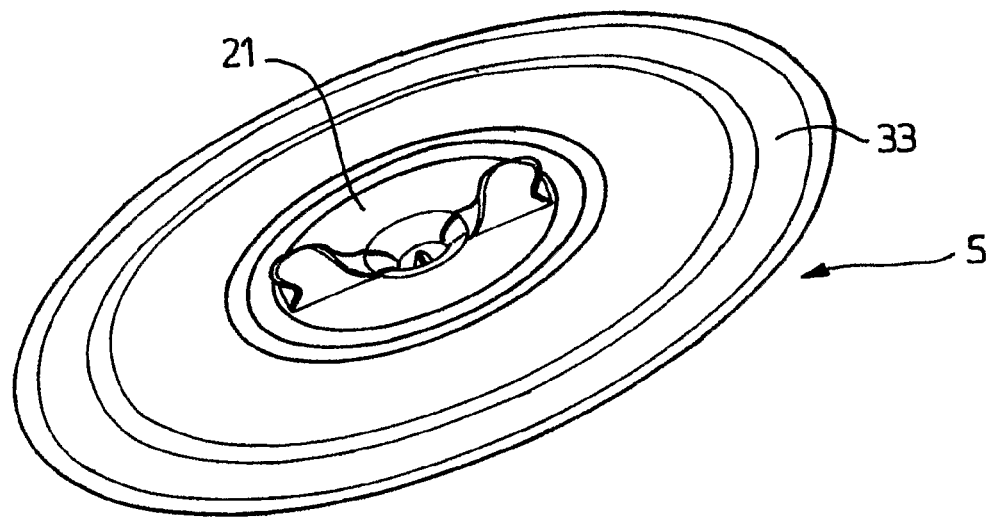
FIG. 5 shows the disposable part of the liquid droplet plug and spray system according to the present invention.

The disposable part further comprises a reservoir constituting a compartment for containing a liquid substance that is to be expelled from the liquid droplet spray plug and spray system as a spray of droplets. As can be seen in FIG. 5, reservoir 33 is connected to and surrounds valve body 21. Reservoir 33 preferably is of the form, fill and seal type, and may be made of any suitable material for this purpose. Examples of such materials are polyethylene or polypropylene. The reservoir may also be for example of an airless type, or a solid type.

Figure 4:
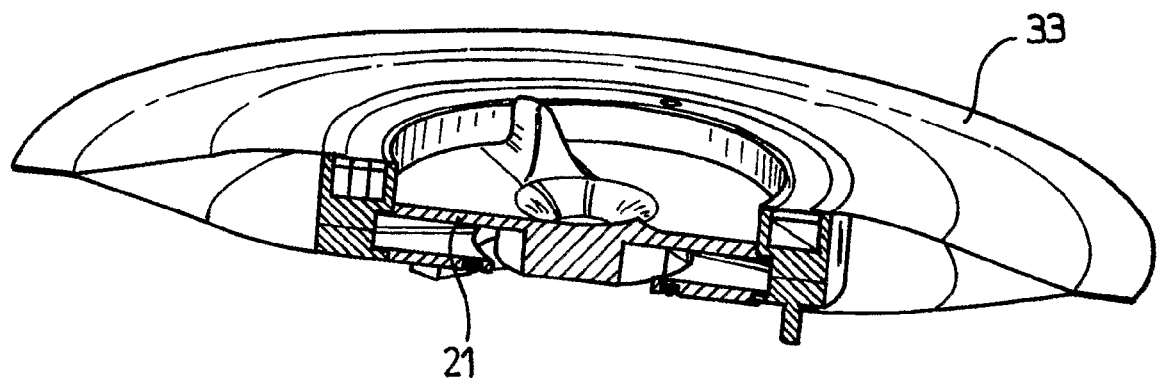
FIG. 4 shows a cross-sectional view of the reservoir attached to the valve body.

Advantageously, reservoir 33 may be divided into two sub-compartments which each may contain a different liquid substance. For example, one sub-compartment may contain a perfume to be dispensed from the system, whereas the other sub-compartment may contain a cleansing liquid to rinse the system after expelling the perfume. Such sub-compartments may be separated one from the other in a known manner such as by a membrane placed in the reservoir. FIG. 4 shows a cross-sectional view of reservoir 33 attached to valve body 21. Reservoir 33 is attached to valve body 21 in a sealed manner to allow liquid to flow from reservoir 33 into the valve body depending on the rotational positioning of cylinder member 22 of the valve body with respect to outer rings 23 and 24, i.e. depending on the fact whether the valve is in its open position or in its closed position. As an example of the sealing of reservoir to the valve body, ultrasound welding may be used. The reservoir may be filled after having been attached to the valve body.

FIG. 5 shows a general view of the disposable part of the liquid droplet plug and spray device according to the present invention. Assembling of the plug and spray system is as follows. The disposable part, hereafter referenced by numeral 3, thus includes valve body 21 and reservoir 33 and is fitted to permanent part 2 by inserting projections 31 into rivets 15 and by inserting notches 30 into grooves 19a, 19b. When fitted, the electronic control means arranged on permanent part 2 are electrically connected with electrode 13 and membrane actuator 7 so as to allow activation of the electromechanical actuator 11.

Figure 6:
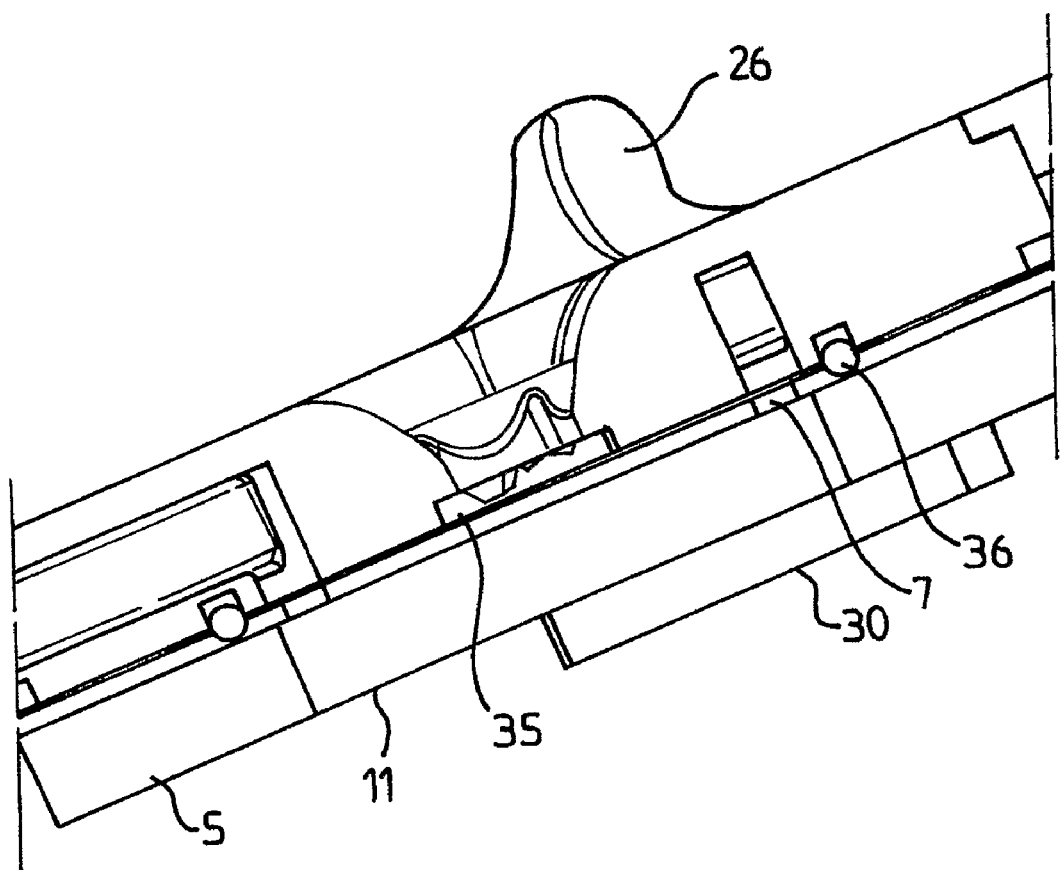
FIG. 6 shows a detailed view of the assembled plug and spray system according to the present invention.

Further, by rotating disposable part 3, a fluid compression chamber, indicated by space 35, is created, as shown in the detailed view of FIG. 6, between membrane actuator 7 on permanent part 2 and nozzle body 28 on disposable part 3. By further turning manipulating member 26 of valve body 21, the fluidic channels 32 will be aligned with apertures 25 of ring members 23, 24 thus allowing the liquid substance contained in reservoir 33 to flow into space 35.

Thus, space 35 forms together with nozzle body 28 and membrane actuator 7 a liquid droplet spray device for expelling the received liquid substance as a spray of droplets in a manner well known from other devices designed by the present Applicant and as described for example in document EP 1 236 517.

To ensure liquid tightness of the assembled plug and spray system, a seal 36, for example a gasket, seal is preferably provided between valve body 21 and membrane actuator 7, as shown in FIG. 6. To this effect, a circular groove may be provided in the bottom surface of valve body 21 for receiving a circular seal 36. When assembled, gasket 36 presses against membrane actuator 7 thus ensuring liquid tightness. Such seal may also be a seal provided by bi-injection moulding.

When activated, electromechanical actuator will vibrate membrane actuator 7 which will cause any liquid present in space 35 between the membrane actuator and the nozzle body to undergo a vibration and to contact nozzle body 28 thereby traversing the nozzles as a liquid droplet spray. Thus, the spray will be ejected from the top surface of valve body 21, as shown in FIG. 6.

Figure 7A:
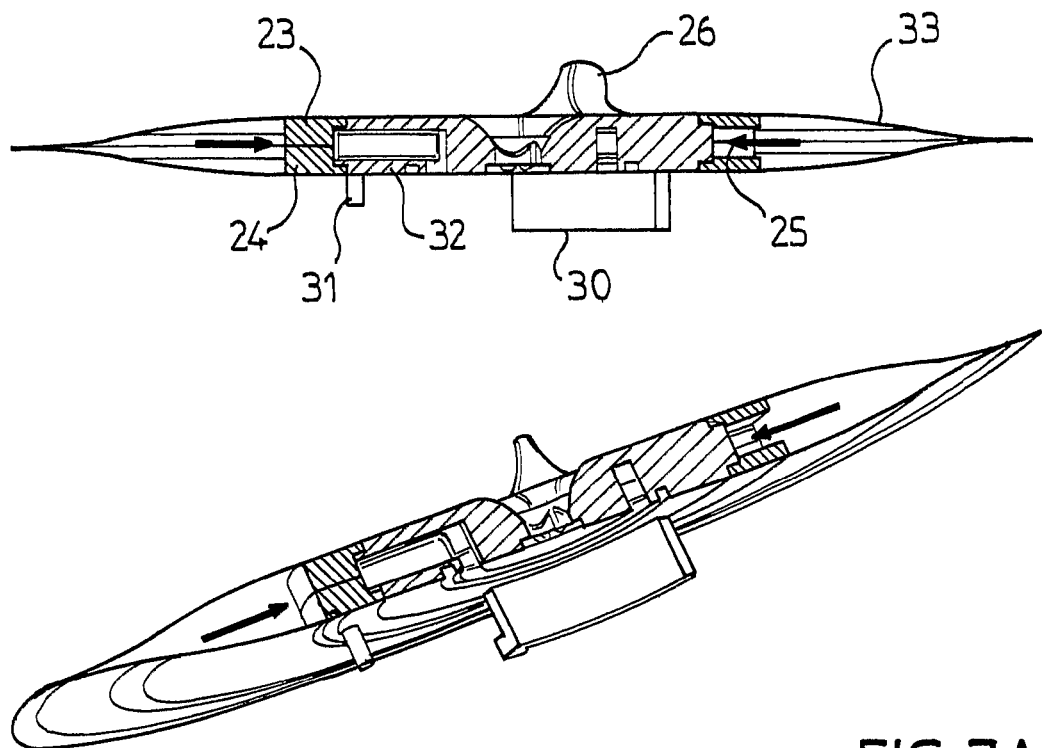
FIG. 7 shows the operation of opening and closing the valve body of the disposable part.
Figure 7B:
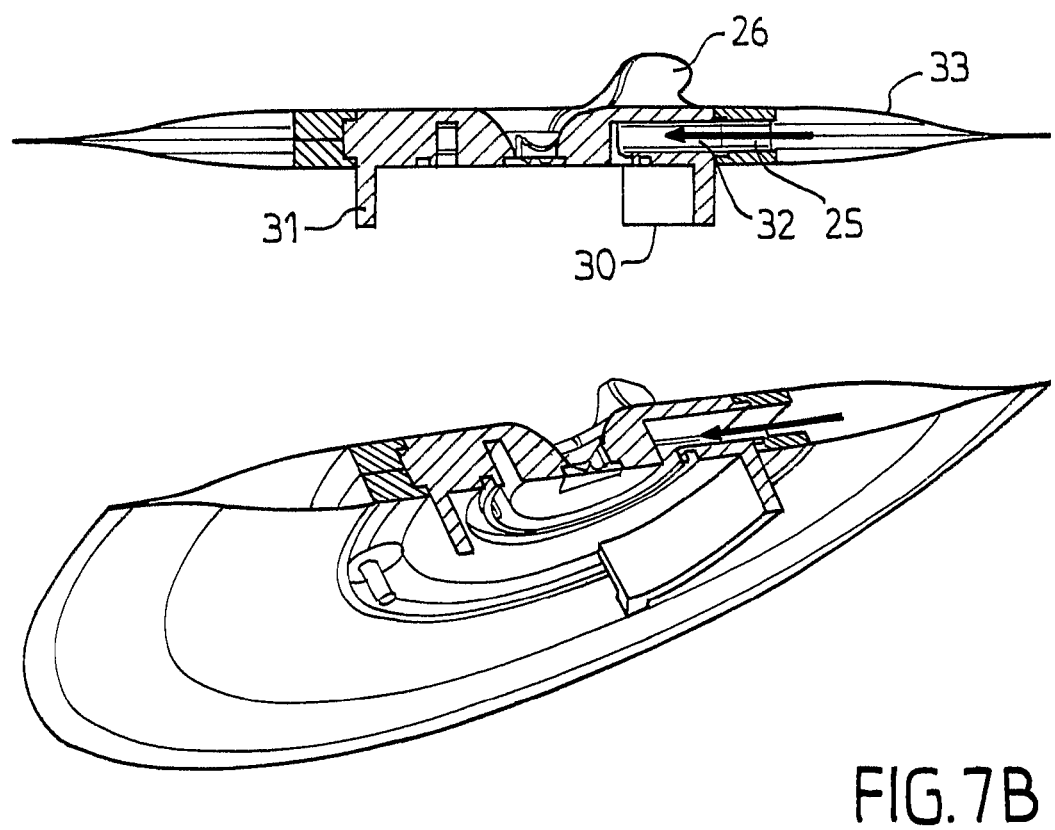

The opening and closing of the fluidic channels in valve body 21 will now be explained while referring to FIG. 7. FIG. 7a shows a cross-sectional view of the liquid droplet spray system S according to the present invention where the valve is in the closed position. When inserting disposable part 3 into permanent part 2, the notches 30 enter grooves 19a, 19b such that any liquid substance contained within reservoir 33 is prevented from entering valve body 21 due to the non-alignment of fluidic channel 32 of cylinder member 22 with aperture 25 of ring members 23, 24. As shown in FIG. 7b, after rotating cylinder member 22 by turning manipulating member 26, notches 30 slide along grooves 19a, 19b, until fluidic channel 32 is aligned with aperture 25. Liquid may now flow from reservoir 33 into valve body 21 where it will reach space 35. By activating electromechanical actuator means 11, the liquid will undergo a vibration and be expelled as a spray of droplets.

Fluidic channel 32 may further contain a soft porous medium, connected on one side to space 35, to facilitate flow of liquid from a reservoir 33 to space 35.

In a preferred arrangement, when turning manipulating member 26 so as to open the valve, when notches 30 reach the end of grooves 19a, 19b, an electronic contact may be made which will automatically activate the electromechanical actuation means so as to trigger the spraying.

Figure 8A:
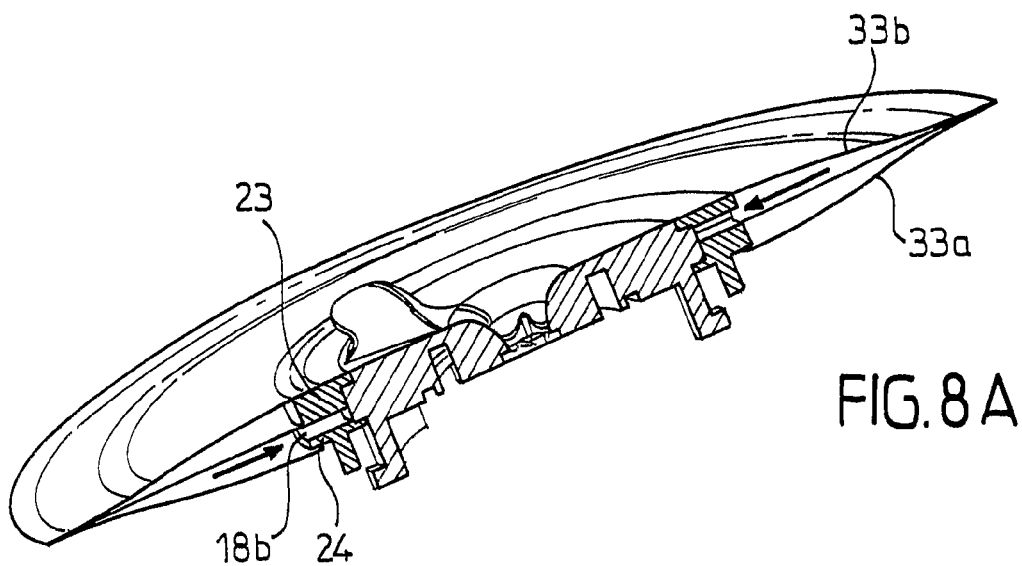
FIG. 8 shows an alternative arrangement of FIG. 7 where the reservoir comprises two sub-compartments.
Figure 8B:
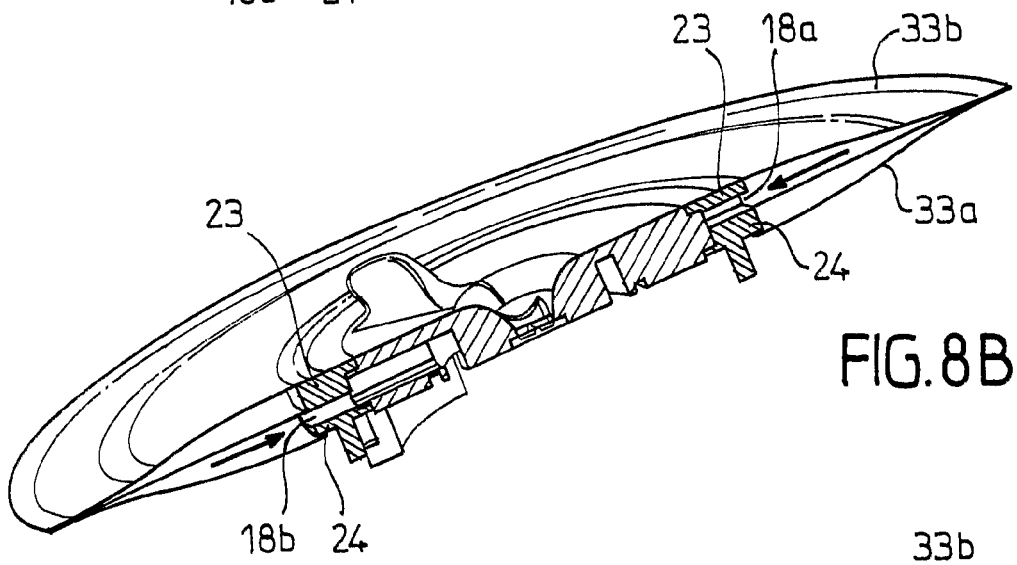
Figure 8C:
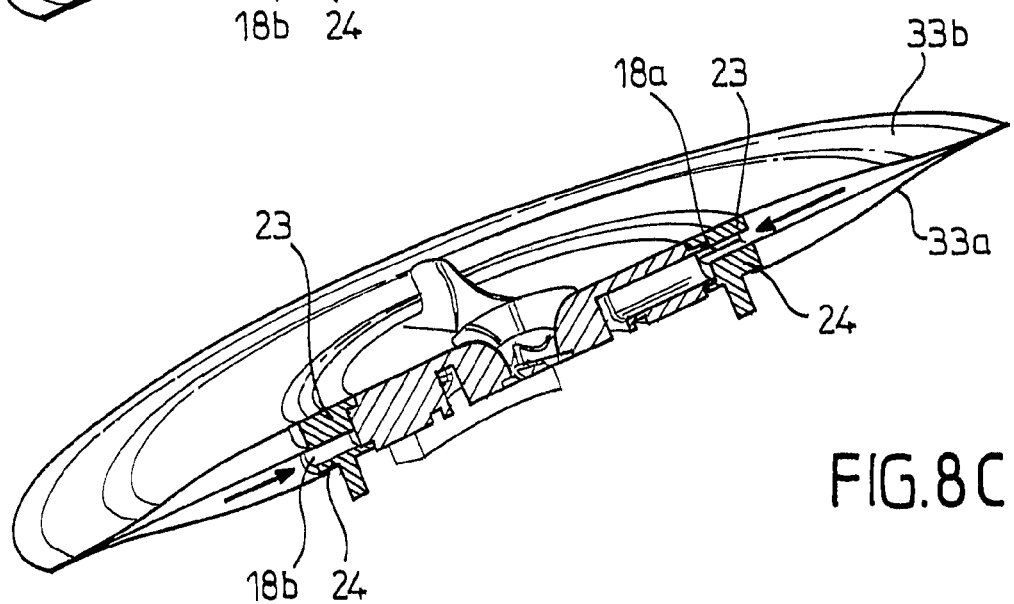

When using the above-mentioned sub-compartments in reservoir 33 that each contain a liquid substance, ring members 23 and 24 should have their slots 18a and 18b arranged such as to allow flow from one sub-compartment at a time into fluidic channel 32 of valve body 21. This can be achieved by having slots 18 arranged along the outer periphery of top ring member 23 shifted along the periphery with respect to slots 18 of bottom ring member 23 so that only one of these upper and lower slots may be aligned with a fluidic channel 32. FIG. 8 shows an example of such an arrangement. Two sub-compartments 33a and 33b are provided. In FIG. 8a, both sub-compartments are closed, i.e. none of the fluidic channels are aligned with slots 18 so that no liquid can flow from a reservoir into valve body 21. In FIG. 8b, after turning the cylinder member 22, lower sub-compartment 33a is opened due to the alignment of a fluidic channel with a slot 18a of bottom ring member 24. Thus, liquid substance contained in sub-compartment 33a may flow into valve body 21 and thus into space 35 to be expelled as a spray. By further turning cylinder member 22, lower sub-compartment 33a is again closed, but upper sub-compartment 33b is now opened by aligning a fluidic channel with a slot 18b of top ring member 23 thus allowing liquid substance to flow from sub-compartment 33b into space 35, as shown in FIG. 8c.

Figure 9:
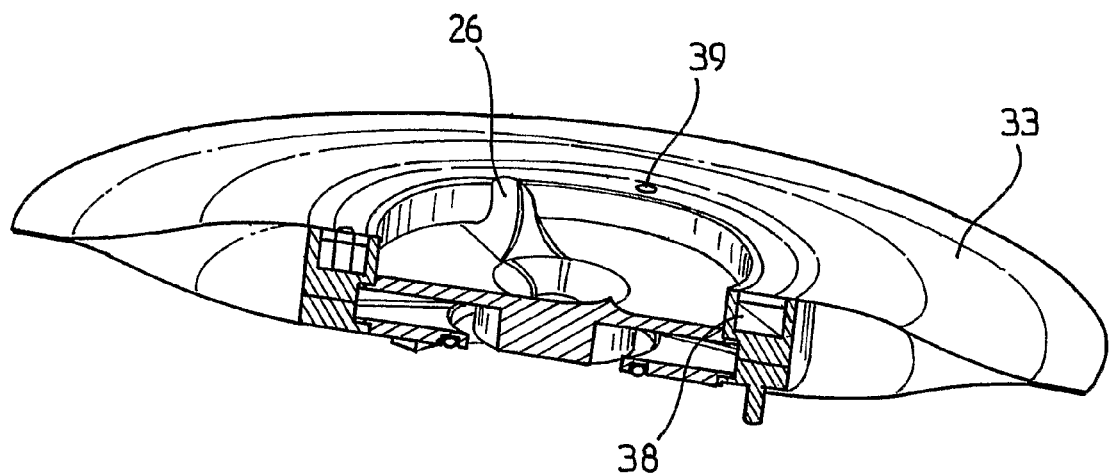
FIG. 9 shows a further alternative arrangement where a powder compartment is provided in a hollow top ring member of the valve body, in a closed valve position.
Figure 10:
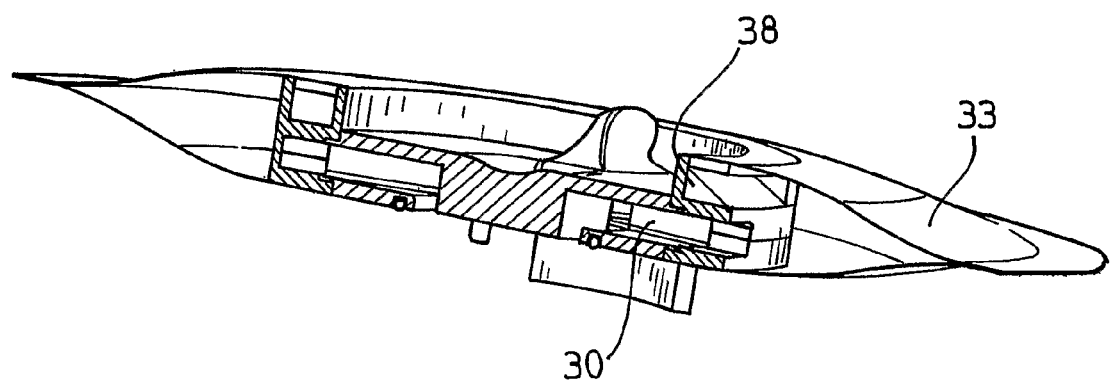
FIG. 10 shows the arrangement of FIG. 9 in an open valve position.

In a further advantageous arrangement, a powder compartment 38 may be provided in the disposable part, for example in top ring member 23 as shown in FIG. 9a. Top ring member 23 is hollow and may have a filling opening 39 on its upper surface allowing filling it with a powder. Such powder may be a medical powder which may mix with a liquid substance in the reservoir to form a desired solution. When the valve is closed, the powder is separated from the liquid substance contained in reservoir 33. However, after turning cylinder member 22 to open the valve, as shown in FIG. 10, the powder can access reservoir 33 to contact the liquid substance so that a mixture may flow into valve body 21 through fluidic channel 32 towards space 35 for spray ejection.

Figure 11:
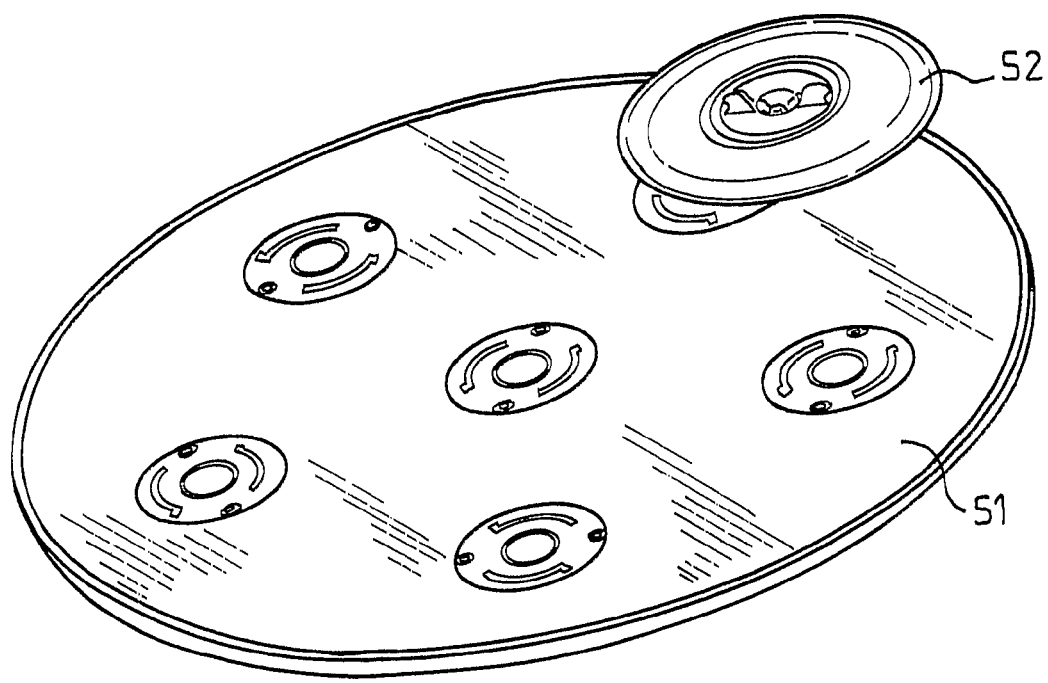
FIG. 11 shows an alternative embodiment of the permanent part.
Figure 11:
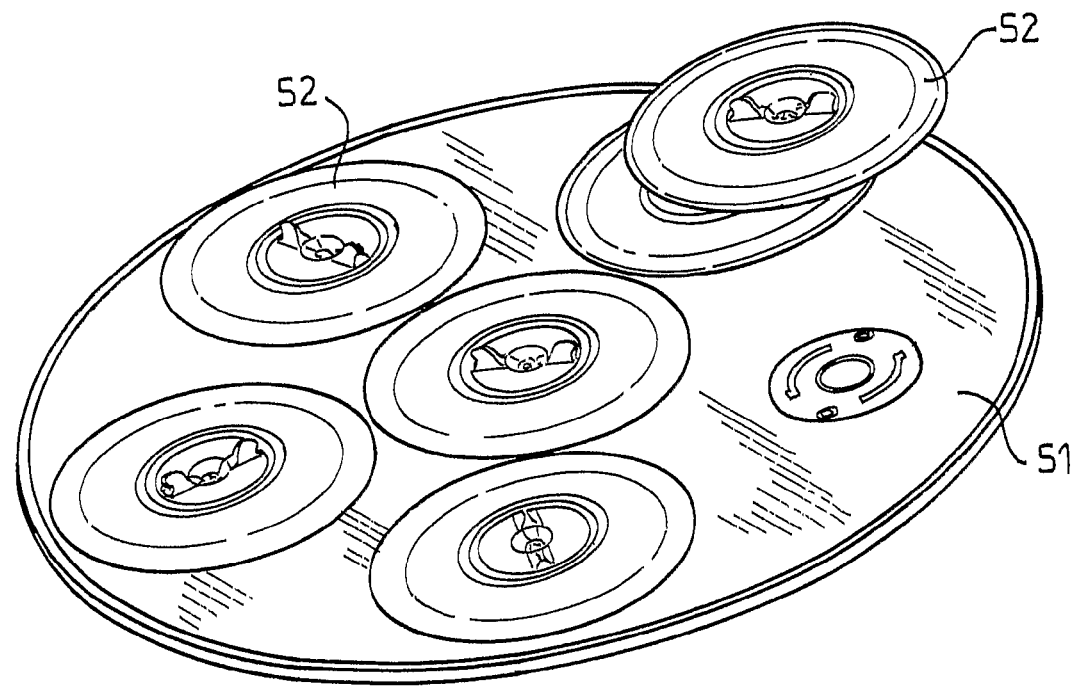
Figure 12:
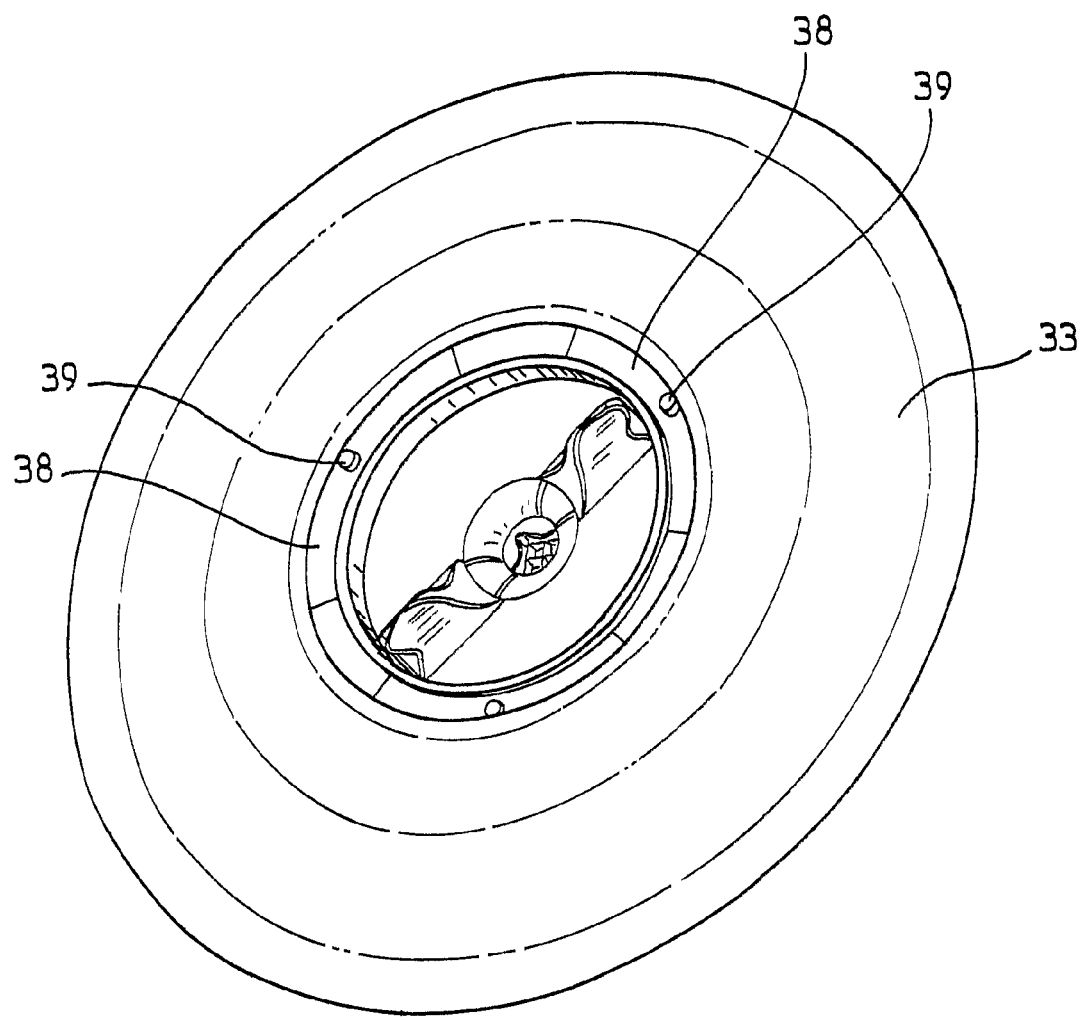
FIG. 12 shows schematically an example of a multiple powder compartment arrangement in a top ring member of the valve body.

FIG. 11 shows an alternative embodiment of the permanent part 2. The permanent part has a support 51, again a PCB in this example, comprising several, in this example six, different permanent sub-parts each comprising an electrode, an electromechanical actuation means, an insulator and a membrane actuator. As shown, six different disposable parts 52 may be inserted into the corresponding sub-parts of the permanent part, similar to a CD-carousel arrangement. Each disposable part 52 corresponds to a disposable part 3 as described here before. As such, several liquid substances may be combined. For example, if the liquid substances are perfumed fragrances, a mixture of fragrances may thus be obtained. Of course, if each reservoir of a disposable part 52 is again subdivided into two compartments, 12 different fragrances may be mixed. In general, the number of fragrances n thus allows for a number of combinations F according to the formula $F=(n-1)*n/2$.

In a further alternative arrangement, several powder compartments 38, each with their own filling opening 39, may be provided. Naturally, the number of fluidic channels in cylinder member 22 should be adjusted to allow for a corresponding number of mixtures of powders in the powder compartments with the liquid substance in reservoir 33. An example of such a multiple powder compartment is shown schematically in FIG. 12.

In an advantageous arrangement, the power source (not shown) may form part of the disposable part 3 such that it constitutes one part with reservoir 33. The power source, typically a battery, may be suitable joined to but detachable from reservoir and disposable part 3 such that the battery may be thrown away in an ecological manner separate from disposable part 3. For example, a tear-out cardboard may be used as the battery pack attached to reservoir 33. By a suitable assembly of the disposable part 3 and the permanent part 2, the fluidic connection may be made on the top surface of PCB 5, whereas the electrical connection may be made on the bottom surface of PCB 5, for example by way of rivet 15.

Thanks to this arrangement, it is possible to readily remove disposable part 3 from the system, for example when the reservoir is empty or when exchanging a reservoir containing one liquid substance against one with a different liquid substance is required without any leakage of liquid from disposable part 3 or from permanent non-disposable part 2. Further due to the replacement of the nozzle body, a possible clogging of nozzles is totally avoided.

Thanks to the above described features of the present liquid droplet plug and spray system, it is possible to use the system for atomising a liquid substance, such as perfume or medicaments, so that the system can be used for example as a nebuliser, a perfume dispenser, an inhaler, a nasal spray, or an ophthalmologic dispenser, or the like with an easily exchangeable reservoir which does not dispense any liquid substance when not in use.

Having described a preferred embodiment of this invention, it will now be apparent to one of skill in the art that other embodiments incorporating its concept may be used. It is therefore, that this invention should not be limited to the disclosed embodiment, but rather should be limited only by the scope of the appended claims.

The invention claimed is:

1. A liquid droplet spray system for atomising a liquid substance including functional liquids, medicated or not, sanitizing or not, fragranced or not, the system comprising:

(a) a support having a central aperture, wherein the support further comprises a plurality of semicircular slots formed therein;

(b) a liquid droplet spray device in which a space is provided, wherein the space is arranged to receive said liquid substance, and the liquid droplet spray device includes a nozzle body covering the space so that said liquid substance exits the space of the liquid droplet spray device by traversing the nozzle body and exits the system by traversing the central aperture of the support;

(c) a reservoir for containing said liquid substance;

(d) a valve body for controlling access of said liquid substance from the reservoir to the space, wherein the valve body comprises a fluidic channel arranged to connect the reservoir to the space by way of the valve body thereby conveying liquid substance contained in the reservoir to the space by way of capillary action, wherein the valve body further comprises a bottom surface, and a plurality of engagement notches disposed at a periphery of the bottom surface;

(e) an electromechanical actuator arranged to actuate liquid substance in said space so that the liquid substance undergoes a vibration and contacts the nozzle body thereby traversing the one or more nozzles as a liquid droplet spray; and (f) electronic control means arranged to at least control said electromechanical actuator, wherein said liquid droplet spray system has two parts that include a first, disposable part in which said reservoir, said valve body, and said nozzle body, are arranged, and a second, non-disposable part in which said support, said electromechanical actuator and said electronic control means are arranged so that said reservoir does not directly contact said fluidic channel, and wherein said valve body ensures that said first, disposable part is liquid tight when not in use, and wherein said plurality of semicircular slots of said support are arranged to receive said engagement notches of said valve body so as to form joining and locking means allowing attachment of the disposable part to the non-disposable part.

2. A liquid droplet spray system according to claim 1, further comprising:

(g) a membrane actuator arranged between said electromechanical actuator and said space.

3. A liquid droplet spray system according to claim 2, wherein said fluidic channel contains a soft porous medium capable of facilitating the conveying of said liquid substance.

4. A liquid droplet spray system according to claim 1, wherein said disposable part further comprises a power source.

5. A liquid droplet spray system according to claim 4, wherein the electronic control means are arranged to allow the system to be automatically started or stopped when inserting or removing said disposable part comprising the power source.

6. A liquid droplet spray system according to claim 4, wherein said power source is removably attached to said reservoir.

7. A liquid droplet spray system according to claim 1, wherein said support is a flexible electric circuit board.

8. A liquid droplet spray system according to claim 1, wherein said support is a printed circuit board.

9. A liquid droplet spray system according to claim 1, wherein said reservoir comprises one more sub-compartments, each sub-compartment containing a liquid substance.

10. A liquid droplet spray system according to claim 1, wherein said disposable part further comprises a powder compartment for containing a powder and wherein a dose of a liquid and powder mixture is releasable from said reservoir.

11. A liquid droplet spray system according to claim 1, wherein said reservoir is selected from the group consisting of a form reservoir, a fill and seal type reservoir, an airless type reservoir, and a solid type reservoir.

12. A liquid droplet spray system according to claim 2, wherein said disposable part further comprises a power source.

13. A liquid droplet spray system according to claim 9, wherein said disposable part further comprises a power source.

14. A liquid droplet spray system according to claim 3, wherein said disposable part further comprises a power source.

15. A liquid droplet spray system according to claim 5, wherein said power source is removably attached to said reservoir.

* * * * *